(12) United States Patent
Karasic

(10) Patent No.: US 6,805,127 B1
(45) Date of Patent: Oct. 19, 2004

(54) INTUBATION PROTECTION DEVICE

(75) Inventor: Brian Lee Karasic, P.O. Box 300547, Houston, TX (US) 77230-0547

(73) Assignee: Brian Lee Karasic, Houston, TX (US)

( * ) Notice: Subject to any disclaimer, the term of this patent is extended or adjusted under 35 U.S.C. 154(b) by 110 days.

(21) Appl. No.: 10/210,731

(22) Filed: Aug. 1, 2002

Related U.S. Application Data

(63) Continuation-in-part of application No. 09/625,528, filed on Mar. 26, 2001.

(51) Int. Cl.[7] ................................................. A61C 5/14
(52) U.S. Cl. ....................... 128/861; 600/237; 600/239; 600/240; 433/93; 433/138; 433/6
(58) Field of Search ................................ 128/898, 859, 128/861; 433/138, 139, 140, 148, 149, 93, 94, 19, 6; 600/237, 238, 239, 240

(56) References Cited

U.S. PATENT DOCUMENTS

| 2,061,936 A | * | 11/1936 | Engelfried ................. 600/237 |
| 2,587,245 A | * | 2/1952 | Terre ........................... 600/238 |
| 2,669,988 A | | 2/1954 | Carpenter .................... 128/136 |
| 4,270,531 A | | 6/1981 | Blachly ................. 128/207.14 |
| 4,425,911 A | | 1/1984 | Luomanen ............. 128/200.26 |
| 4,887,965 A | * | 12/1989 | Fox ............................. 433/140 |
| 4,991,566 A | * | 2/1991 | Shulman et al. ............ 600/213 |
| 5,347,996 A | * | 9/1994 | Huan ......................... 600/238 |
| 5,590,643 A | | 1/1997 | Flam ..................... 128/200.26 |
| 5,623,924 A | | 4/1997 | Linderman ............. 128/207.17 |

* cited by examiner

Primary Examiner—Henry Bennett
Assistant Examiner—Centu Nguyen

(57) ABSTRACT

The invention is a multipurpose intra-oral device made of a fastener, a first mouthguard connected to the fastener, wherein the first mouthguard has a first mouthguard base engaging a top tooth, a first mouthguard buccal surface, a first mouthguard lingual surface and a first mouthguard occlusal surface, a second mouthguard connected to the fastener, wherein the second mouthguard has a second mouthguard base to engage a bottom tooth, a second mouthguard buccal side, a second mouthguard lingual side and a second mouthguard occlusal surface, at least one first tube connected to one of the mouthguards surface, and at least one first post connected to the other of the mouthguard surface for engaging the tube.

32 Claims, 6 Drawing Sheets

INTUBATION PROTECTION DEVICE

The present application is a continuation-in-part application of co-pending patent application Ser. No. 09/625,528 filed Mar. 26, 2001.

FIELD OF THE INVENTION

This invention generally relates to a multipurpose intra-oral device that can be inserted in the mouth of a patient to gain access to the mouth and throat of the patient.

BACKGROUND OF THE INVENTION

Presently there is no device that protects the upper and lower dentition, helps to direct the endotracheal tube into the trachea and helps to visualize the pharyngeal area. There has been a commonly fabricated mouthguard device which is used for several purposes, (1) protection for upper and lower teeth especially while sleeping to prevent damage from grinding and clenching, (2) protect upper and lower teeth while playing any sports where an object or another person might cause damage to the persons teeth, and (3) relaxation of the musculature of the face from bruxing, and thereby protect against myofacial pain dysfunction and even reduce possible damage to temperomandibular joint (TMJ). However, these uses for conventional mouthguards do not make them useful to open the mouth sufficiently to provide a 12.5 to 15 mm opening for a child's throat, and a 17.0 mm to 21.0 mm opening for an adult throat, which permits the endotracheal tube to easily extend into the trachea. Furthermore, for many years, there has been a need for an intubation protection device that helps to protect the upper and lower dentition from damage during the use of the laryngoscope and other similar devices, and a device which helps the physician to visualize the back of the throat for improved operational function.

Devices known in the prior art are in U.S. Pat. Nos. 4,270,531, 4,425,911, 5,623,924, 5,590,643, and 2,669,988. None of these devices provide the flexibility of the present device with a detachable tongue retractor feature, a detachable throat opener, as well as separately engagable and sizable wedges to connect to the respective mouthguards for enabling many different sizes of mouths and types of operations to be accommodated.

SUMMARY OF THE INVENTION

The invention is a multipurpose intra-oral device made of a fastener, two mouthguards, a tube, and at least one post. Each mouthguard is connected to a fastener and engages a tooth and the buccal, lingual, and occlusal surface of the mouthguard. The tube is connected to one of the mouthguard's surfaces. A post is connected to the other mouthguard's surface for engaging the tube.

The invention is also the above multipurpose intra-oral device made of two fasteners, two mouthguards, a second mouthguard, a first tube and a first post.

The invention is a method for intubating a patient by inserting a tube down a patient's throat. The method involves opening the patient's mouth, inserting the multipurpose intra-oral device over the residual ridge, opening the multipurpose intra-oral device by adjusting the fasteners to an open position, insert a throat opener into the channels of the multipurpose intra-oral device, opening the throat. Next, the method involves inserting a tongue retractor into the tongue retractor holder, depressing the tongue, and inserting a tube into the patient's throat.

The invention is a method for illuminating a patient's throat. The method includes opening the patient's mouth having a tongue, inserting a multipurpose device into the patient's mouth and over the residual, opening the multipurpose intra-oral device by adjusting the fastener to an open position, inserting a throat opener into the channels of the multipurpose intra-oral device, and opening the throat with the throat opener.

Next, the method involves inserting the tongue retractor into the tongue retractor holder, depressing the tongue, and illuminating the patient's throat.

DETAILED DESCRIPTION OF THE PREFFERED EMBODIMENTS

Figure 1:
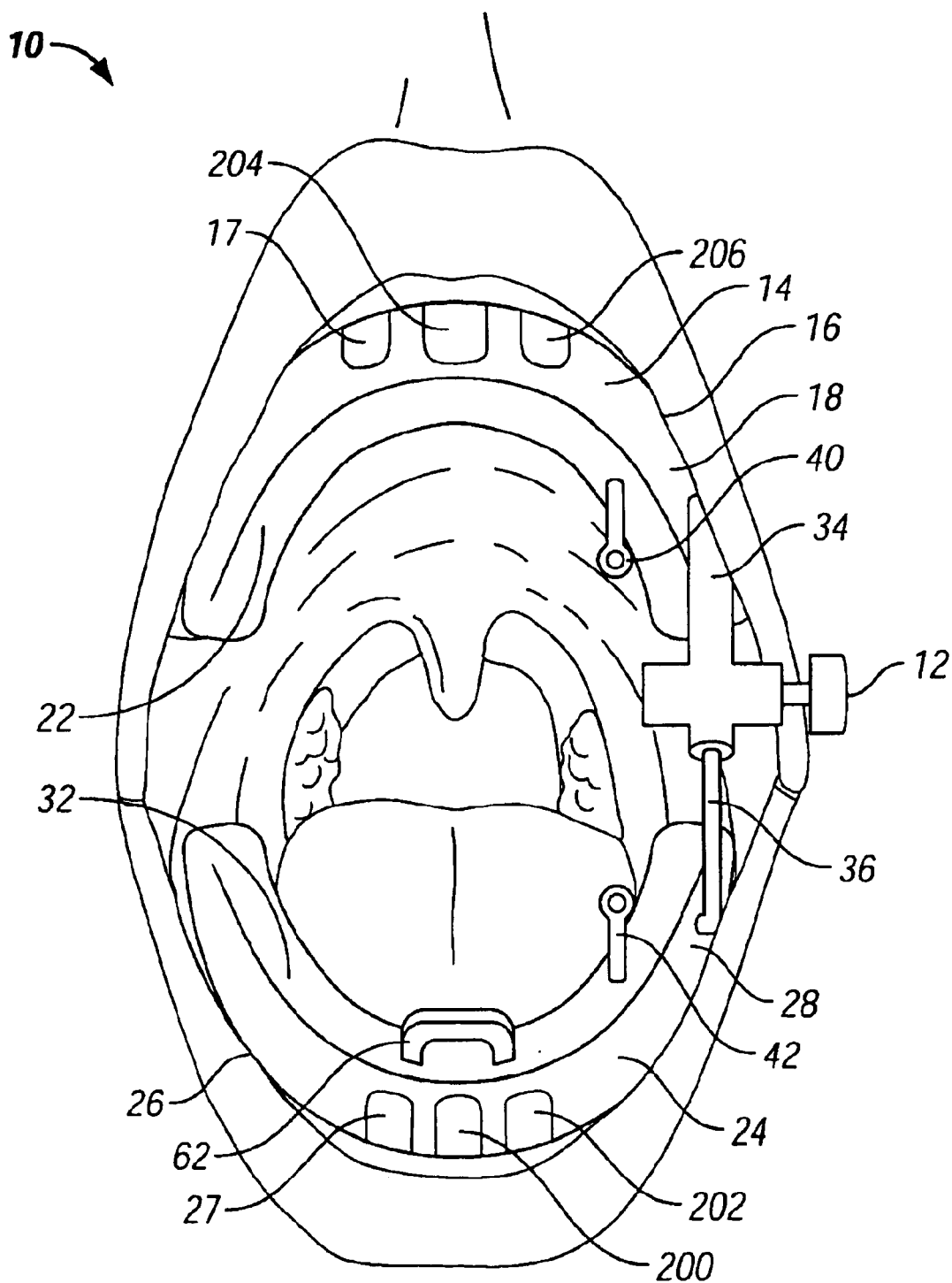
FIG. 1 is a frontal view of the device for use on one side of the mouth.

The multipurpose intra-oral device (10) comprising: a fastener (12), a first mouthguard (14), a second mouthguard (24), at least one first tube (34) and at least one first post (36). The first mouthguard (14) connects to the fastener (12), wherein the first mouthguard has a first mouthguard base (16), which engages a top tooth (17), a first mouthguard buccal surface (18), a first mouthguard lingual surface (20) and a first mouth mouthguard occlusal surface (22). The second mouthguard (24) connects to the fastener (12), wherein the second mouthguard has a second mouthguard base (26), which engages a bottom tooth (27), a second mouthguard buccal side (28), a second mouthguard lingual side (30) and a second mouthguard occlusal surface (32). The device has at least one first tube (34) connected to one of the mouthguard surfaces and at least one first post (36) connected to the other side of the mouthguard surface for engaging the tube.

FIG. 1 shows the frontal view of the invention as a multipurpose intra-oral device (10) for use in the patient's mouth having a first mouthguard (14) and a second mouthguard (24). The first mouthguard (14) having a first mouthguard base (16), a first mouthguard buccal surface (18) and a first mouthguard occlusal surface (22). The second mouthguard (24) having a second mouthguard base (26), a second mouthguard buccal side (28) and a second mouthguard occlusal surface (32). A first channel (40) is disposed on the occlusal surface of the first mouthguard and the second channel (42) disposed on the occlusal surface of the second mouthguard for engaging a throat opener. The multipurpose intra-oral device further comprising a tongue retractor holder (62) mounted to the second mouthguard (24). Each occlusal surface has a surface for engaging the patient's teeth. In FIG. 1, the upper teeth are (17), (204) and (206), and the lower teeth are shown as (27), (200) and (202). The embodiment of the device is a first fastener (12) comprising one tube (34) and one post (36).

The multipurpose intra-oral device, wherein each of the mouthguards engage a plurality of teeth. In the preferred embodiment of the invention the mouthguards are made from material, which is elastomeric. Preferably the mouthguards are made from molded material. The mouthguards are made from a member of the group, rigid acrylic material: such as, molloplast-B, nickel chromium, Vitallium 2000, chromium cobalt and combinations thereof.

In the present invention the posts, fasteners and tubes made from rigid material. Preferably the posts, fasteners and tubes are made from an acrylic polymer.

The multipurpose intra-oral device contains mouthguards that are custom molded to a patient's teeth. Therefore, the mouthguards are made from self-molding material.

Figure 2:
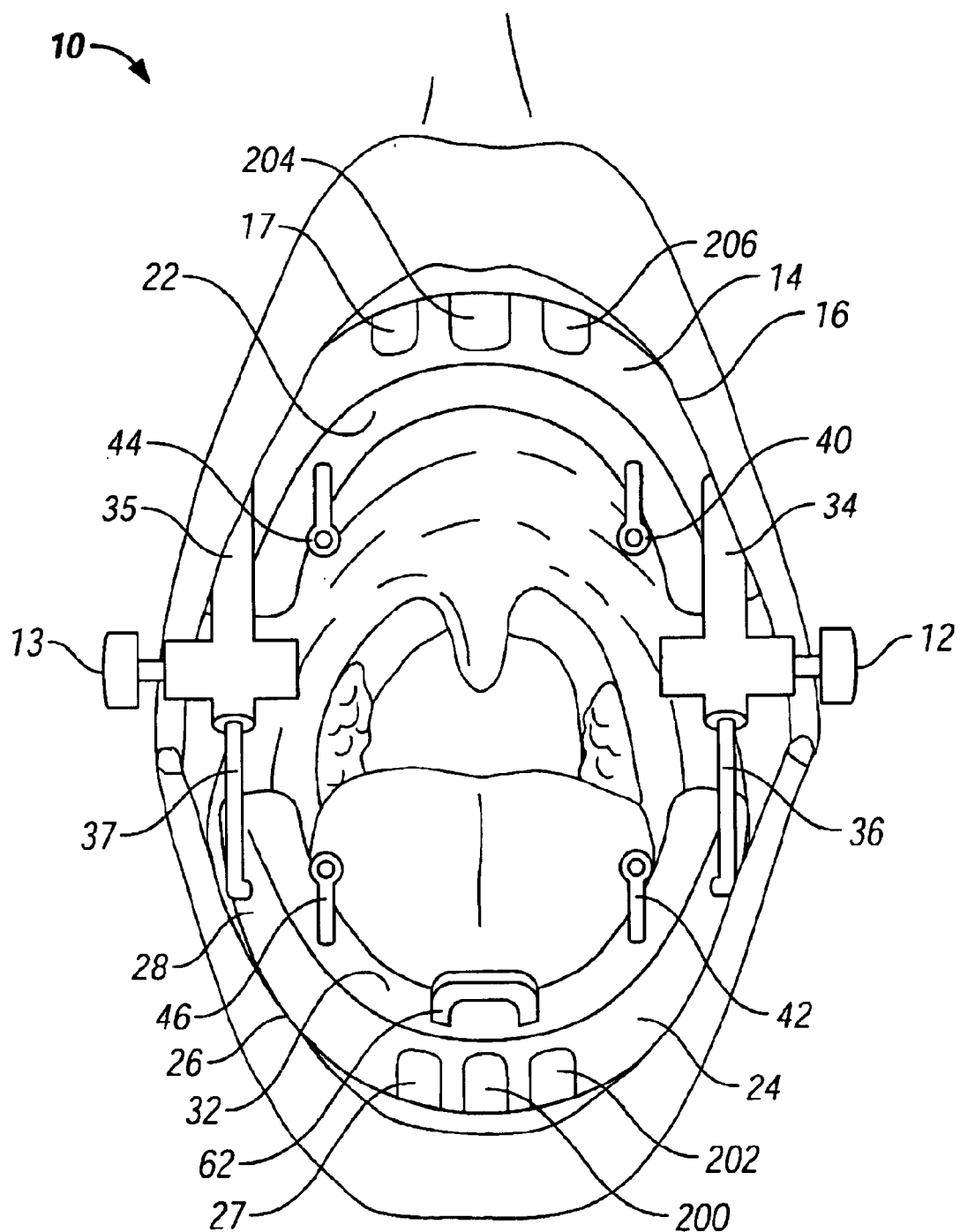
FIG. 2 is a frontal view of the device for use in the full mouth.

FIG. 2 is similar to FIG. 1 and shows the frontal view of the invention as a multipurpose intra-oral device (10) for use in the patient's mouth having a first mouthguard (14) and a second mouthguard (24). The first mouthguard (14) having a first mouthguard base (16), a first mouthguard buccal surface (18) and a first mouthguard occlusal surface (22). The second mouthguard (24) having a second mouthguard base (26), a second mouthguard buccal side (28) and a second mouthguard occlusal surface (32). A first channel (40) is disposed on the occlusal surface of the first mouthguard and the second channel (42) is disposed on the occlusal surface of the second mouthguard for engaging a throat opener. The multipurpose intra-oral device further comprising a tongue retractor holder (62) mounted to the second mouthguard (24). Each occlusal surface has a surface for engaging the patient's teeth. FIG. 2 shows a lower tooth (27) and an upper tooth (17). A third channel (44) is disposed on the occlusal surface of the first mouthguard and a fourth channel (46) is disposed on the occlusal surface of the second mouthguard. The most preferred embodiment of the device is a first fastener (12) and second fastener (13). The first fastener comprises one tube (34) and one post (36). The second fastener comprises a second tube (35) and a second post (37).

In the present invention the first mouthguard is a maxillary mouthguard and second mouthguard is a mandibular mouthguard.

The multipurpose intra-oral device preferably comprises: a first fastener (12) and a second fastener (13), a first mouthguard (14), a second mouthguard (24), a first and second tube (34 and 35) and a first and second post (36 and 37). The first mouthguard (14) connects to the first fastener (12) and the second fastener (13), wherein the first mouthguard (14) has a first mouthguard base (16) engaging a top tooth (17), a first mouthguard buccal surface (18), a first mouthguard lingual surface (20) and a first mouthguard occlusal surface (22). The second mouthguard (24) connects to the first fastener (12) and the second fastener (13), wherein the second mouthguard (13) has a second mouthguard base (26) to engage a bottom tooth (27), a second mouthguard buccal side (28), a second mouthguard lingual side (30) and a second mouthguard occlusal surface (32). The first tube (34) and the second tube (35) are connected to one of the mouthguards surface. While, the first post (36) and the second post (37) are connected to the other end of the mouthguard surface for engaging the tubes.

The most preferred embodiment of the multipurpose intra-oral device is when the fastener comprises of at least a first fastener (12) mounted on the first mouthguard (14) and at least a second fastener (13) mounted on the first mouthguard (14). Preferably using between 4 and 6 fasteners to engage the mouthguards.

The invention further comprises a first channel (40) disposed on the occlusal surface of the first mouthguard and a second channel (42) disposed on the occlusal surface of the second mouthguard for engaging a throat opener. The first and second channels each comprise a first wall, a second wall and a passageway connecting the first and second walls. The first channel (40) and a third channel (44) are disposed on the occlusal surface of the first mouthguard, and a second channel (42) and fourth channel (46) are disposed on the occlusal surface of the second mouthguard for engaging a throat opener.

In the present invention a tongue retractor holder (62) is most preferably mounted to the mouthguard engaging the bottom tooth for engaging a tongue retractor for suppressing tongue movement. The tongue retractor holder can be a rectangular shaped arch, or it can be a U-shaped arch for slidably engaging the tongue depressor.

The post is connected to the buccal surface of the first mouthguard and the tube is connected to the buccal surface of the second mouthguard, and wherein the post and the tube are in an opposing relationship. Most preferably the post is connected to the lingual surface of the first mouthguard and the tube is connected to the lingual surface of the second mouthguard. The post and the tube are then in an opposing relationship. The post is also preferably connected to the occlusal surface of the first mouthguard and the tube is connected to the occlusal surface of the second mouthguard. Therefore, the post and tube are in an opposing relationship.

In the present invention the posts, fasteners and tubes made from rigid material. Preferably the posts, fasteners and tubes are made from an acrylic polymer.

Figure 3:
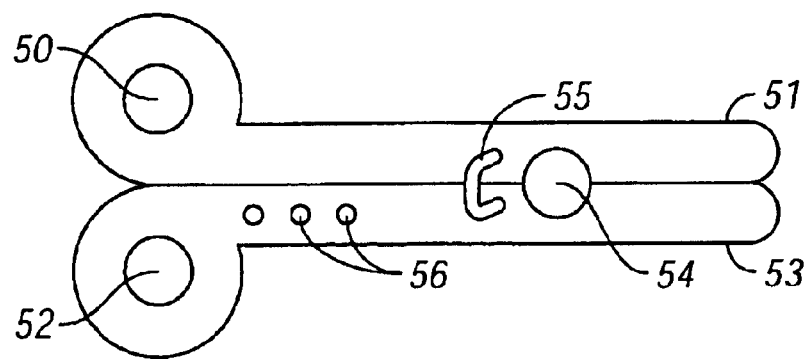
FIG. 3 is a hinge embodiment of fastener.

FIG. 3 is a hinge embodiment of the fastener. The preferred embodiment of the fastener is comprised of: a first finger holder (50), a first arm (51), a second finger holder (52), a second arm (53), a first pin (54), a lever (55) and a stopping hole (56).

The fastener (12) consists of a hinge for connecting the tube to the post for modifying the space between the mouthguards. The hinge has a first finger holder (50) engaging a first arm (51) and a second finger holder (52) engaging a second arm (53). The first and second arm are connected by a first pin (54) and a lever (55), for engaging a stopping hole (56) to enable the hinge to be stopped open.

Figure 4:
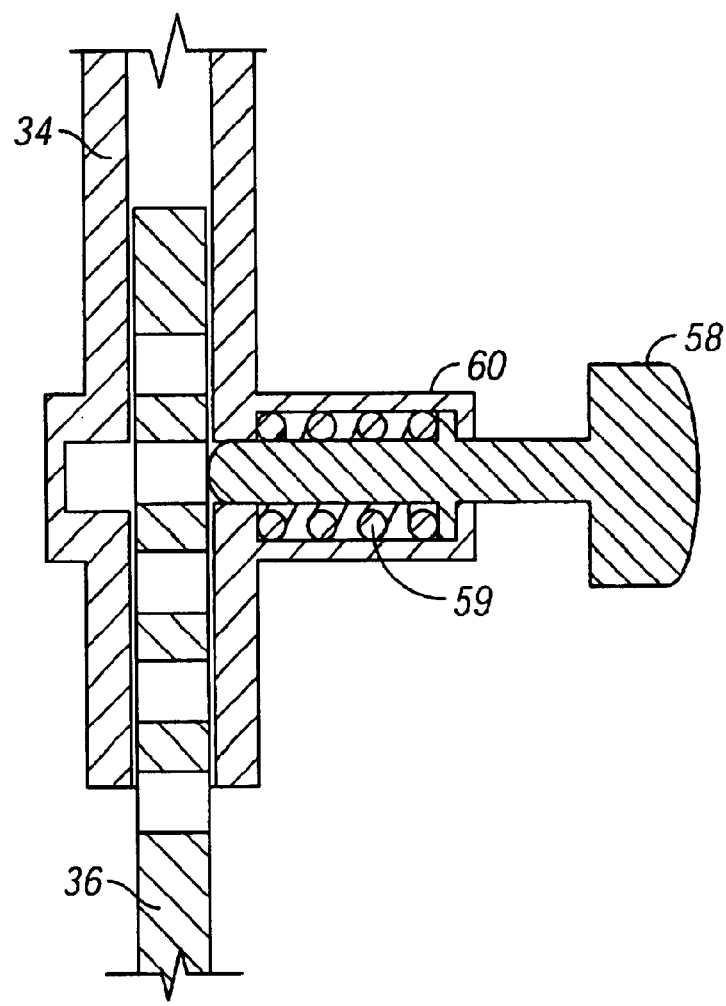
FIG. 4 is a threaded screw (ratchet) version of fastener.

The invention requires a threaded post (59) with a finger engagement surface (58) that secures into a threaded housing (60) as shown in FIG. 4. The threaded housing attaches to the first post (36). The first post is also attached to the first tube (34).

In the preferred embodiment the fastener is spring-loaded and consists of a threaded screw device for connecting the tube to the post. This modifies the space between the mouthguards. Having an finger engagement surface (58) connected to a threaded post (59) for engaging a threaded housing (60), wherein the threaded post can be screwed inwardly at an angle of 90 degrees to the post (36) to stop movement of the post.

Figure 5:
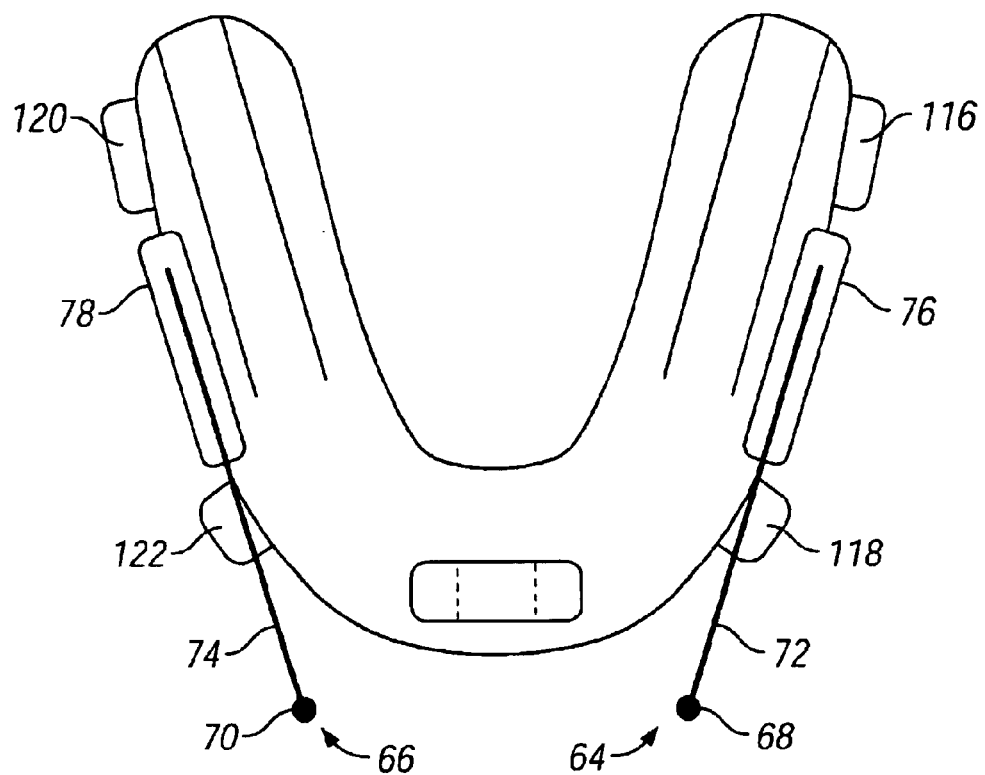
FIG. 5 is a top view of the device showing the ratchet fastener.

FIG. 5 is a top view of the device showing the ratchet fastener. The multipurpose intra-oral device comprises a first scanner holder (116) that can also contain an additional holder for a camera, light attachment and or digital scanner and a second scanner holder (118) for engaging an intra-oral digital scanner as shown on one side of the mouth in FIG. 5. The first ratchet device (64) comprises a first finger engagement (68) connected to the first connector arm (72) for adjustment mechanisms for the fastener. The connector arm is then attached to the first ratchet hinge (76) that is a connector to the fastener. The other side of the ratchet fastener contains a third scanner holder (120) and a fourth scanner holder (122). The second ratchet device (66) comprises a second finger engagement (70) connected to the second connector arm (74), which connects to the second ratchet hinge (78).

The multipurpose intra-oral device further comprises a first scanner holder (116) and a second scanner holder (118) for engaging an intra-oral digital scanner. The third scanner (120) and a fourth scanner (122) are also for engaging an intra-oral digital scanner on the opposite side of the mouth.

Figure 6:
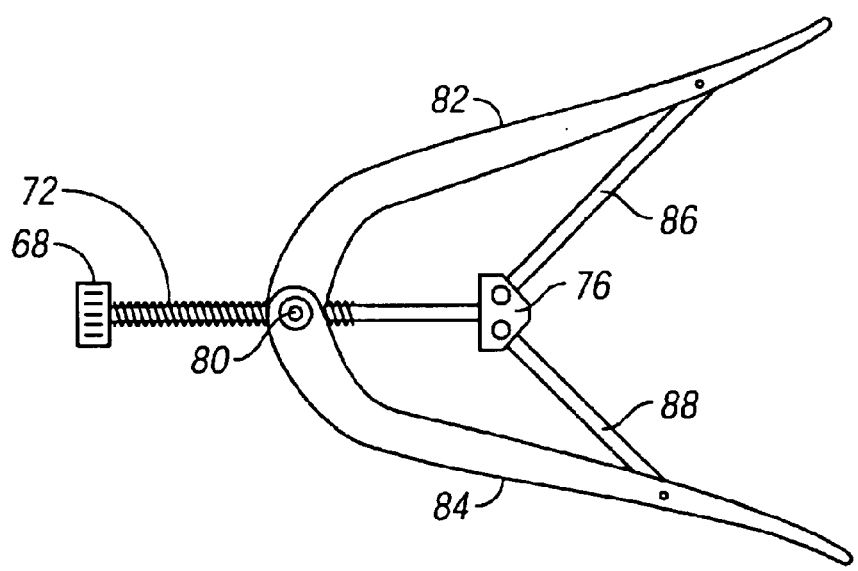
FIG. 6 is a detailed top view of the ratchet fastener.

FIG. 6 is a top view of the ratchet fastener in detail of the multipurpose intra-oral device. Most preferably having a first support arm (82) and a second support arm (84) that is connected with a second pin (80). The first support arm engages the first hinge arm (86) and second support arm engages the second hinge arm (88). The first and second hinge arms engage the ratchet hinge (76) that is operated by the connector arm (72) having a finger engagement (68).

Figure 7:
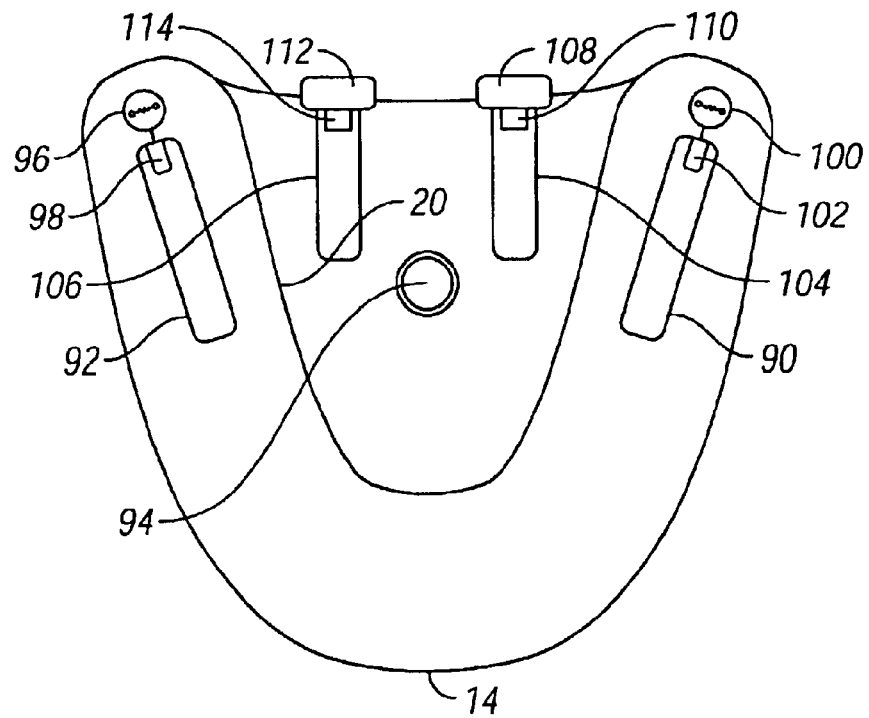
FIG. 7 is a top view of the upper segment of the intra-oral device showing the light source and camera features.

The invention further comprises of at least one light source. FIG. 7 shows a detailed view of the upper sequent of the intra-oral device that shows the light source and camera features. In the preferred embodiment there is preferably a first light source (90) and a second light source (92). The first light source is constructed with a first light source ball (100) mounted to a first light source socket (102). The second light source is mounted to a second light source ball (96) engaged with a second light source socket (98). The battery (94) powers the light sources. The light sources are located on the first mouthguard (14) along with channels for the throat retractors. The first video camera (104) is mounted on the mouthguard opposite from the second video camera (106). The first video camera (104) is mounted to a first camera ball (108) and a first camera socket (110) enabling the video camera to be oriented in any direction. The second video camera (106) is mounted to a second camera ball (112) and a second camera socket (114).

The most preferred embodiment comprises of at least one light source (90) and a second light source (92), as shown in FIG. 7, mounted on one of the mouthguards. The multipurpose intra-oral device uses a battery (94) to power the light source, wherein the battery can be disposed on one of the mouthguards.

The light source can be a fiber optic light source. The light source in the invention, is preferably mounted to a first light source ball (100) and a first light source socket (102). The ball and socket enable the light source to be oriented in any direction.

The invention consists of a first video camera (104) and can use a second video camera (106), as shown in FIG. 7, mounted on the mouthguards. The first video camera is mounted to a first camera ball (108) and the first camera socket (110) enabling the video camera to be oriented in any direction. The second video camera (106) can be mounted to a second camera ball (112) and a second camera socket (114), which also enables the video camera to be oriented in any direction.

Figure 8:
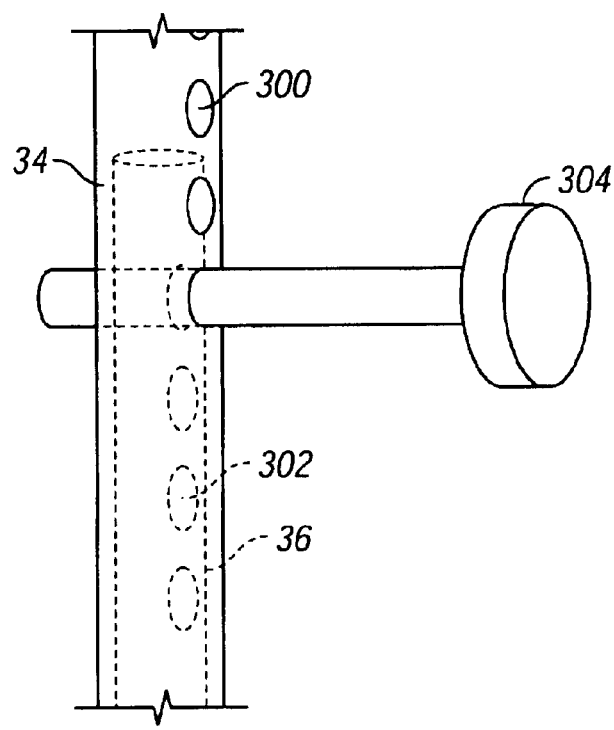
FIG. 8 is a side view of a pin stop embodiment for the device.

As shown in FIG. 8, a side view of the pin stop embodiment of the invention, the tube has at least one tube stop hole (300) and the post has at least one post stop hole (302). The tube stop holes can be aligned with the post stop holes and a stop pin (304) can engage the holes and stops closure of the device.

Figure 9:
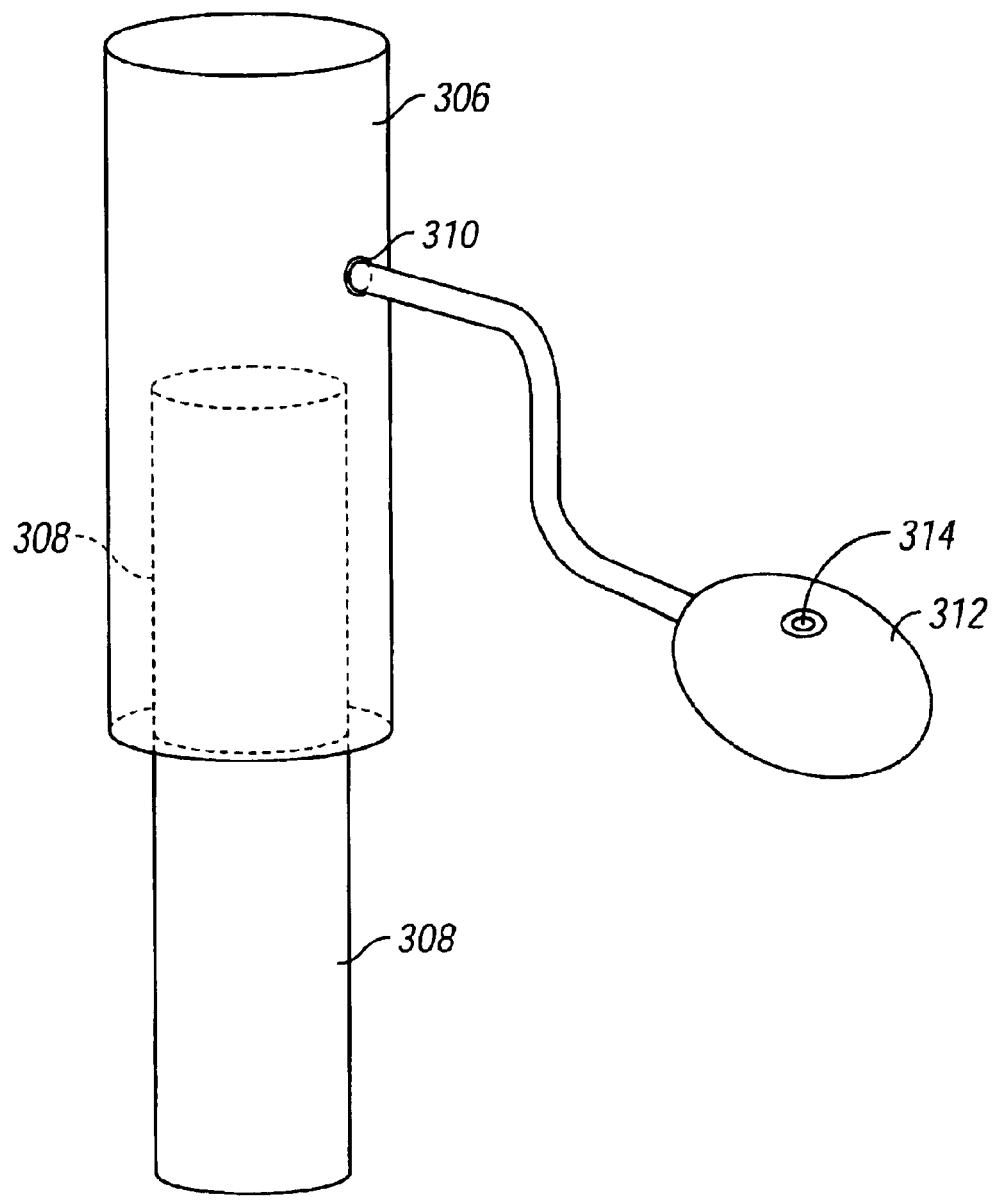
FIG. 9 shows a pneumatic embodiment of the device with the post and tube.

FIG. 9 shows a pneumatic embodiment of the device with the post and tube. A first pneumatic tube (306) is connected to a second pneumatic tube (308). The first and second pneumatic tubes are in a slidable engagement, and a port (310) connected to a compressed air source (312) and a release button (314) to release pressurized air from the tube and post engagement.

The fastener can be a pneumatic controlled mechanism connected to the tube and the post for operably engaging the tube with the post in a controlled pneumatic manner for quick release. The pneumatic controlled mechanism compromises: a first pneumatic tube (306) connected to a second pneumatic tube (308), wherein the first and second pneumatic tubes are in a slidable engagement. The mechanism also supports a port (310) connected to a compressed air source (312) and a release button (314), which releases pressurized air from of the tube and the post engagement.

A method for intubating a patient by inserting a tube down a patient's throat comprised in steps. The first step involves opening the patient's mouth having a tongue. Then inserting a multipurpose intra-oral device into the patient's mouth and over at least an upper residual ridge and a lower residual ridge in the patient's mouth. The device comprises: a fastener; a first mouthguard connected to the fastener, wherein the first mouthguard has a first mouthguard base, a first mouthguard buccal surface, a first mouthguard lingual surface and a first mouthguard occlusal surface, a second mouthguard connected to the fastener, wherein the second mouthguard has a second mouthguard base, a second mouthguard buccal side, a second mouthguard lingual side and a second mouthguard occlusal surface; at least one tube connected to one of the mouthguards surface; and at least one post connected to the other of the mouthguard surfaces for engaging the tube. Then opening the multipurpose intra-oral device by adjusting the fastener to an open position. Inserting a throat opener into the channels of the multipurpose intra-oral device. Opening the throat with the throat opener and inserting a tongue retractor into the tongue retractor holder, depressing the tongue and lastly, inserting a tube into the patient's throat.

A method for illuminating a patient's throat comprised in steps. Opening the patient's mouth having a tongue and inserting a multipurpose device into the patient's mouth and over at least an upper residual ridge and a lower residual ridge in the patient's mouth. Opening the multipurpose intra-oral device by adjusting the fastener to an open position and inserting a throat opener into the channels of the multipurpose intra-oral device. The throat is then opened with a throat and a tongue retractor is inserted into the tongue retractor holder, depressing the tongue and illuminating the patient's throat.

While this invention has been described with emphasis on the preferred embodiments, it should be understood that within the scope of the appended claims, the invention might be practiced other than as specifically described herein.

What is claimed is:

1. A multipurpose intra-oral device comprising:
   a. a fastener;
   b. a first mouthguard connected to the fastener, wherein said first mouthguard has a first mouthguard base engaging a top tooth, a first mouthguard buccal surface, a first mouthguard lingual surface and a first mouthguard occlusal surface;
   c. a second mouthguard connected to the fastener, wherein said second mouthguard has a second mouthguard base to engage a bottom tooth, a second mouthguard buccal side, a second mouthguard lingual side and a second mouthguard occlusal surface;
   d. at least one first tube connected to one of said mouthguards surface; and
   e. at least one first post connected to the other of said mouthguard surface for engaging said tube.

2. The multipurpose intra-oral device of claim 1, wherein each of said mouthguard engages a plurality of teeth.

3. The multipurpose inter-oral device of claim 1, wherein the fastener consists of a hinge for connecting said tube to said post for modifying the space between the mouthguards, wherein said hinge has a first finger holder engaging a first arm and a second finger holder engaging a second arm wherein said first and second arms are connected by a first pin a lever for engaging a stopping hole to enable the hinge to be stopped open.

4. The multipurpose intra-oral device of claim 1, wherein the fastener consists of a threaded screw device for connecting said tube to said post for modifying the space between the mouthguards having an finger engagement surface connected to a threaded post for engaging a threaded housing wherein said threaded post can be screwed inwardly at an angle of 90 degrees to said post to stop movement of said post.

5. The multipurpose intra-oral device of claim 1, wherein the fastener is a pneumatic controlled mechanism connected to said tube and said post for operably engaging said tube with said post in a controlled pneumatic manner for quick release, comprising: a first pneumatic tube connected to a second pneumatic tube, wherein the first and second pneumatic tubes are in a slidable engagement, and a port connected to a compressed air source, a release button to release pressurized air from of said tube and post engagement.

6. The multipurpose intra-oral device of claim 1, wherein said fastener is a ratchet device having a first support arm and a second support arm connected with a pin and the first support arm engages first hinge arm and second support arm engages second hinge arm, the first and second hinge arms engage ratchet hinge that is operated by connector arm having a finger engagement.

7. The multipurpose intra-oral device of claim 1, further comprising at least one light source mounted on one of said mouthguards.

8. The multipurpose intra-oral device of claim 7, further wherein said light source is powered by a battery.

9. The multipurpose intra-oral device of claim 8, wherein said battery is disposed on one of the mouthguards.

10. The multipurpose intra-oral device of claim 7, wherein said light source is mounted to a first light source ball and a first light source socket connector enabling the light source to be oriented in any direction.

11. The multipurpose intra-oral device of claim 7, wherein said light source is a fiber optic light source.

12. The multipurpose intra-oral device of claim 1, further comprising a first video camera mounted on one of the mouthguards.

13. The multipurpose intra-oral device of claim 12, wherein said video camera is mounted to a first camera ball and first camera socket enabling the video camera to be oriented in any direction.

14. The multipurpose intra-oral device of claim 1, further comprising a first scanner holder and a second scanner holder for engaging an intra-oral digital scanner.

15. The multipurpose intra-oral device of claim 1, wherein said first mouthguard is maxillary and second mouthguard is mandibular mouthguard.

16. A multipurpose intra-oral device comprising:
   a. a first fastener and a second fastener;
   b. a first mouthguard connected to the first fastener and the second fastener, wherein said first mouthguard has a first mouthguard base engaging a top tooth, a first mouthguard buccal surface, a first mouthguard lingual surface and a first mouthguard occlusal surface;
   c. a second mouthguard connected to the first fastener and the second fastener, wherein said second mouthguard has a second mouthguard base to engage a bottom tooth, a second mouthguard buccal side, a second mouthguard lingual side and a second mouthguard occlusal surface;
   d. a first tube and a second tube connected to one of said mouthguards surface; and
   e. a first post and a second post connected to the other of said mouthguard surface for engaging said tubes.

17. The multipurpose intra-oral device of claim 16 wherein said fastener comprises at least a first fastener mounted on the first mouthguard and an at least a second fastener mounted on the first mouthguard.

18. The multipurpose intra-oral device of claim 16, further comprising a first channel disposed on the occlusal surface of the first mouthguard and a second channel disposed on the occlusal surface of the second mouthguard for engaging a throat opener.

19. The multipurpose intra-oral device of claim 18, wherein said first and second channels each comprise a first wall, a second wall and a passageway connecting said first and second walls.

20. The multipurpose intra-oral device of claim 16, further comprising a first channel and a third channel disposed on the occlusal surface of the first mouthguard, and a second channel and fourth channel disposed on the occlusal surface of the second mouthguard for engaging a throat opener.

21. The multipurpose intra-oral device of claim 16, further comprising a tongue retractor holder mounted to the mouthguard engaging the bottom tooth for engaging a tongue retractor for suppressing tongue movement.

22. The multipurpose intra-oral device of claim 21, wherein said tongue retractor holder is a rectangular shaped arch for slidably engaging the tongue depressor.

23. The multipurpose intra-oral device of claim 21, wherein said tongue retractor holder is a U-shaped arch for slidably engaging the tongue depressor.

24. The multipurpose intra-oral device of claim 16, wherein said tube has at least one tube stop hole and said post has at least one post stop hole, and wherein said tube stop hole can be aligned with said post stop holes and a stop pin can engaging the holes and stop closure of the device.

25. The multipurpose intra-oral device of claim 16, wherein said post is connected to the buccal surface of said first mouthguard and said tube is connected to the buccal surface of said second mouthguard, and wherein said post and said tube are in an opposing relationship.

26. The multipurpose intra-oral device of claim 16, wherein said mouthguards are made from material that is elastomeric.

27. The multipurpose intra-oral device of claim 16, wherein said mouthguards are made from a member of the group, rigid acrylic material, nickel chromium, chromium cobalt and combinations thereof.

28. The multipurpose intra-oral device of claim 16, wherein said mouthguards are made from molded material.

29. The multipurpose intra-oral device of claim 16, wherein said posts, fasteners, and tubes made from rigid material.

30. The multipurpose intra-oral device of claim 28, wherein said posts, fasteners, and tubes are made from an acrylic polymer.

31. The multipurpose intra-oral device of claim 16, wherein said mouthguards are custom molded to a patient's teeth.

32. The multipurpose intra-oral device of claim 16, wherein said mouthguards are made from self-molding material.

* * * * *